US008728139B2

(12) United States Patent
Azure et al.

(10) Patent No.: US 8,728,139 B2
(45) Date of Patent: May 20, 2014

(54) SYSTEM AND METHOD FOR ENERGY DELIVERY TO A TISSUE USING AN ELECTRODE ARRAY

(75) Inventors: Larry Azure, La Conner, WA (US); Charles E. Hill, Issaquah, WA (US); Andrew L. Azure, Mount Vernon, WA (US)

(73) Assignees: LaZure Technologies, LLC, La Conner, WA (US); LaZure Scientific, Inc., Issaquah, WA (US)

( * ) Notice: Subject to any disclaimer, the term of this patent is extended or adjusted under 35 U.S.C. 154(b) by 450 days.

(21) Appl. No.: 12/761,915

(22) Filed: Apr. 16, 2010

(65) Prior Publication Data

US 2011/0060393 A1  Mar. 10, 2011

Related U.S. Application Data

(60) Provisional application No. 61/170,085, filed on Apr. 16, 2009.

(51) Int. Cl.
*A61N 1/04* (2006.01)

(52) U.S. Cl.
USPC ............... 607/109; 607/36; 607/37; 607/96; 607/98; 607/2; 607/115

(58) Field of Classification Search
USPC ................. 607/36, 37, 96, 98, 109, 115, 2
See application file for complete search history.

(56) References Cited

U.S. PATENT DOCUMENTS

| | | | |
|---|---|---|---|
| 3,991,770 | A | 11/1976 | LeVeen |
| 4,016,886 | A | 4/1977 | Doss et al. |
| 4,346,715 | A | 8/1982 | Gammell |
| 4,448,198 | A | 5/1984 | Turner |
| 4,676,258 | A | 6/1987 | Inokuchi et al. |
| 4,732,161 | A | 3/1988 | Azam et al. |
| 4,763,671 | A | 8/1988 | Goffinet |
| 4,821,725 | A | 4/1989 | Azam et al. |
| 4,860,752 | A | 8/1989 | Turner |
| 5,277,201 | A | 1/1994 | Stern |
| 5,370,677 | A | 12/1994 | Rudie et al. |
| 5,472,441 | A | 12/1995 | Edwards et al. |
| 5,630,426 | A | 5/1997 | Eggers et al. |
| 5,681,282 | A | 10/1997 | Eggers et al. |
| 5,807,395 | A | 9/1998 | Mulier et al. |
| 5,810,804 | A | 9/1998 | Gough et al. |
| 5,827,276 | A | 10/1998 | LeVeen et al. |
| 5,855,576 | A | 1/1999 | LeVeen et al. |
| 5,868,740 | A | 2/1999 | LeVeen et al. |
| 5,935,123 | A | 8/1999 | Edwards et al. |
| 5,957,922 | A | 9/1999 | Imran |
| 5,968,041 | A | 10/1999 | Edwards |
| 6,050,992 | A | 4/2000 | Nichols |
| 6,071,280 | A | 6/2000 | Edwards et al. |

(Continued)

OTHER PUBLICATIONS

Aoyagi et al., "Effects of Moderate Hyperthermia on the Rabbit Sacroma Model," Neurol. Med. Chir. (Tokyo) 43:105-111 (2003).

(Continued)

*Primary Examiner* — Joseph Stoklosa
(74) *Attorney, Agent, or Firm* — Wilson Sonsini Goodrich & Rosati

(57) ABSTRACT

Devices, systems, and related methods for electric fields delivery for preferential destruction of cancerous cells and tissue ablation.

19 Claims, 13 Drawing Sheets

(56) References Cited

U.S. PATENT DOCUMENTS

| | | | |
|---|---|---|---|
| 6,090,105 | A | 7/2000 | Zepeda et al. |
| 6,136,020 | A | 10/2000 | Faour |
| 6,148,236 | A | 11/2000 | Dann |
| 6,212,433 | B1 | 4/2001 | Behl |
| 6,231,570 | B1 | 5/2001 | Tu et al. |
| 6,337,998 | B1 * | 1/2002 | Behl et al. ............ 607/101 |
| 6,402,742 | B1 | 6/2002 | Blewett et al. |
| 6,419,653 | B2 | 7/2002 | Edwards et al. |
| 6,440,127 | B2 | 8/2002 | McGovern et al. |
| 6,477,426 | B1 | 11/2002 | Fenn et al. |
| 6,517,534 | B1 | 2/2003 | McGovern et al. |
| 6,537,272 | B2 | 3/2003 | Christopherson et al. |
| 6,682,555 | B2 | 1/2004 | Cioanta et al. |
| 6,738,663 | B2 | 5/2004 | Schroeppel et al. |
| 6,743,226 | B2 | 6/2004 | Cosman et al. |
| 6,835,864 | B2 | 12/2004 | Luck |
| 6,850,804 | B2 | 2/2005 | Eggers et al. |
| 6,866,624 | B2 | 3/2005 | Chornenky et al. |
| 6,868,289 | B2 | 3/2005 | Palti |
| 6,939,346 | B2 | 9/2005 | Kannenberg et al. |
| 6,944,504 | B1 | 9/2005 | Arndt et al. |
| 6,958,064 | B2 | 10/2005 | Rioux et al. |
| 6,993,394 | B2 | 1/2006 | Eggers et al. |
| 6,994,706 | B2 | 2/2006 | Chornenky et al. |
| 7,016,725 | B2 | 3/2006 | Palti |
| 7,053,063 | B2 | 5/2006 | Rubinsky et al. |
| 7,089,054 | B2 | 8/2006 | Palti |
| 7,135,029 | B2 | 11/2006 | Makin et al. |
| 7,136,699 | B2 | 11/2006 | Palti |
| 7,146,210 | B2 | 12/2006 | Palti |
| 7,238,182 | B2 | 7/2007 | Swoyer et al. |
| 7,311,708 | B2 | 12/2007 | McClurken |
| 7,333,852 | B2 | 2/2008 | Palti |
| 7,555,345 | B2 * | 6/2009 | Wahlstrand et al. ............ 607/46 |
| 7,824,394 | B2 * | 11/2010 | Manstein ............ 606/9 |
| 7,917,222 | B1 * | 3/2011 | Osorio et al. ................ 607/45 |
| 2002/0058933 | A1 | 5/2002 | Christopherson et al. |
| 2002/0077676 | A1 | 6/2002 | Schroeppel et al. |
| 2002/0082610 | A1 | 6/2002 | Cioanta et al. |
| 2003/0130575 | A1 | 7/2003 | Desai |
| 2003/0150372 | A1 | 8/2003 | Palti |
| 2003/0208248 | A1 * | 11/2003 | Carter et al. ............ 607/69 |
| 2004/0068297 | A1 | 4/2004 | Palti |
| 2004/0087939 | A1 | 5/2004 | Eggers et al. |
| 2004/0116952 | A1 | 6/2004 | Sakurai et al. |
| 2004/0176804 | A1 | 9/2004 | Palti |
| 2005/0171523 | A1 | 8/2005 | Rubinsky et al. |
| 2005/0171574 | A1 | 8/2005 | Rubinsky et al. |
| 2005/0209640 | A1 | 9/2005 | Palti |
| 2005/0209641 | A1 | 9/2005 | Palti |
| 2005/0209642 | A1 | 9/2005 | Palti |
| 2005/0222565 | A1 * | 10/2005 | Manstein ............ 606/41 |
| 2005/0240173 | A1 | 10/2005 | Palti |
| 2005/0240228 | A1 | 10/2005 | Palti |
| 2005/0251126 | A1 | 11/2005 | Gellman et al. |
| 2006/0079883 | A1 | 4/2006 | Elmouelhi et al. |
| 2006/0149226 | A1 | 7/2006 | McCullagh et al. |
| 2006/0149341 | A1 | 7/2006 | Palti |
| 2006/0155270 | A1 | 7/2006 | Hancock et al. |
| 2006/0167499 | A1 | 7/2006 | Palti |
| 2006/0206162 | A1 * | 9/2006 | Wahlstrand et al. ............ 607/46 |
| 2006/0217694 | A1 | 9/2006 | Chin et al. |
| 2006/0217703 | A1 | 9/2006 | Chornenky et al. |
| 2006/0233867 | A1 | 10/2006 | Palti |
| 2006/0237019 | A1 | 10/2006 | Palti |
| 2006/0241547 | A1 | 10/2006 | Palti |
| 2006/0241577 | A1 | 10/2006 | Balbierz et al. |
| 2006/0282122 | A1 | 12/2006 | Palti |
| 2007/0135879 | A1 | 6/2007 | McIntyre et al. |
| 2007/0225766 | A1 | 9/2007 | Palti |
| 2008/0033422 | A1 | 2/2008 | Turner et al. |

OTHER PUBLICATIONS

Baronzio and Hager, "Medical Intelligence Unit—Hyperthermia in Cancer Treatment: A Primer," Landes Bioscience and Springer Science+Business Media LLC; ISBN:0-387-33440-8 (2006).

Chan et al., "Electrically Stimulated Cell Membrane Breakdown in Human Placenta TL and Lung Cancer Cell A549 in 3D Trap Arrays on Si Substrate," Device Research Conference, pp. 103-104 (Jun. 23-25, 2003).

Chang, D.C., "Design of protocols for electroporation and electrofusion: Selection of electrical parameters," in D. C. Chang, B. M. Chassy, J. A. Saunders and A. E. Sowers. (Ed.ÆEds.), Guide to electroporation and electrofusion. Academic Press, Inc., San Diego, pp. 429-455 (1992).

Chang, D.C., "Structure and dynamics of electric field-induced membrane pores as revealed by rapid-freezing electron microscopy," in D. C. Chang, B. M. Chassy, J. A. Saunders and A. E. Sowers. (Ed.ÆEds.), Guide to Electroporation and Electrofusion. Academic Press, Inc., San Diego, pp. 9-27 (1992).

Coss et al., "Effects of Hyperthermia (41.5°) on Chinese Hamster Ovary Cells Analyzed in Mitosis," Cancer Research 39:1911-1918 (1979).

Cucullo et al., "Very Low Intensity Alternating Current Decreases Cell Proliferation," GLIA 51:65-72 (2005).

DeFord et al., "Effective Estimation and Computer Ccontrol of Minimum Tumour Temperature During Conductive Interstitial Hyperthermia," Int. J. Hyperthermia 7:441-453 (1991).

Haemmerich and Wood, "Hepatic Radiofrequency Ablation at Low Frequencies Preferentially," Int. J. Hyperthermia 22:563-574 (2006).

Janigro et al., "Alternating Current Electrical Stimulation Enhanced Chemotherapy: a Novel Strategy to Bypass Multidrug Resistance in Tumor Cells," BMC Cancer 6:1-12 (2006).

Kirson et al., "Alternating Electric Fields Arrest Cell Proliferation in Animal Tumor Models and Human Brain Tumors," PNAS 104:10152-10157 (2007).

Kirson et al., "Disruption of Cancer Cell Replicatioin by Alternating Electric Fields," Cancer Res. 64:3288-3295 (2004).

Marmor et al., "Tumor Cure and Cell Survival After Localized Radiofrequency Heating," Cancer Research 37:879-883 (1977).

Miller et al., "Cancer Cells Ablation With Irreversible Electroporation," Technology in Cancer Research & Treatment 4:1-7 (2005).

Oleson et al., "Biological and Clinical Aspects of Hyperthermia in Cancer Therapy," Am J. Clin. Oncol. 11:368-380 (1988).

Pethig, R., "Dielectric Properties of Biological Materials: Biophysical and Medical Applications," IEEE Trans. EI 19(5): 453-473 (1984).

Proskuryakov et al., "Necrosis is an Active and Controlled Form of Programmed Cell Death," Biochemistry (Moscow) 67:387-408 (2002).

Rubinsky et al., "Irreversible Electroporation: a New Ablation Modality—Clinical Implications," Tech. Cancer Res. Treatment 6:1-12 (2007).

Shimm and Gerner, "Hyperthermia in the Treatment of Malignancies," in: Lehman, Justus F., Therapeutic Heat and Cold (Maryland, Williams & Wilkins, 1990), Ch. 14, pp. 674-699. ISBN 0-683-04908-9.

Stix, "Blockbuster—New Understanding of the Biology Behind a Successful Cancer Therapy May Lead to a Drug That Can Treat an Array of Solid Tumors," Scientific American, 294(5): 60-63 (May 2006).

Tello et al., "Electrochemical Therapy to Treat Cancer (In Vivo Treatment)," Proceedings of the 20th Annual International Conference of the IEEE EMBS, pp. 3524-3527 (Aug. 23-26, 2007).

Yi, "Cellular Ion Content Changes During and After Hyperthermia," Biochem. Biophys. Res. Communic. 91:177-182 (1979).

Zimmermann, U., "Electric field-mediated fusion and related electrical phenomena," Biochim Biophys Acta 694(3): 227-277 (1982).

Zimmermann, U., et al. "Transcellular ion flow in *Escherichia coli* B and electrical sizing of bacterias," Biophys. J. 13(10): 1005-1013 (1973).

Zimmermann, U., et al., "Rotation of cells in an alternating electric field: the occurrence of a resonance frequency," Z. Naturforsch [C] 36(1-2): 173-177 (1981).

* cited by examiner

SYSTEM AND METHOD FOR ENERGY DELIVERY TO A TISSUE USING AN ELECTRODE ARRAY

CROSS-REFERENCE TO RELATED APPLICATION

The present invention claims the benefit of priority under 35 U.S.C. §119(e) of U.S. Provisional Application No. 61/170,085, filed Apr. 16, 2009, the entire content of which is incorporated herein by reference.

BRIEF SUMMARY OF THE INVENTION

The present invention relates generally to electric field delivery to a tissue of a patient. More particularly, the present invention provides systems, devices and related methods for electric fields delivery, e.g., for destruction of cancerous cells and tissue ablation.

Tissue heating for cancer tissue hyperthermia includes treatment in which the temperature of either local tissue or the whole body is raised to a therapeutic level for the destruction of tumors. Cancer hyperthermia has been studied for the last several decades, with research often focusing on the combined effects of hyperthermia on cells and other treatments such as ionizing radiation therapy and chemotherapy.

While study results provide promising evidence and rationale supporting application of hyperthermia in cancer treatment, implementation remains difficult. Perhaps the most significant obstacle for practical application of hyperthermia is the generation and accurate control of heating to tumor tissues. Effective temperature ranges are narrow, with excessive temperatures indiscriminately destroying both healthy tissue and tumor tissue alike, and insufficient heating or low temperatures having minimal or no effect. Conventional existing methods for whole body heating include, for example, hot wax, hot air, hot water, fluid perfusion, RF fields and microwaves. However, existing equipment and methodologies have so far been inadequate in delivering accurate and controlled heating to tissues in more optimal temperature ranges, particularly to sub-surface or deep-seated tissues.

Accordingly, there is a continuing interest to develop devices and methods for accurate and controlled heating of tumor tissues and tissues including cancerous cells.

BRIEF SUMMARY OF THE INVENTION

The present invention provides systems, devices and related methods for applying electric fields to a tissue of a patient. Using methods and structures as described herein, current fields or electrical current can be delivered for destruction (e.g., preferential destruction) of cancerous cells and tissue ablation and, where desired, controlled for more precisely delivering a temperature gradient applied to the tissue. Methods and devices of the present invention will generally be designed to advance or control, with use of control module structures and assemblies described herein, an electrode or plurality of electrodes to a target tissue region and apply an electric field to the target tissue region. The electrode or plurality thereof can be positioned such that the applied electric field extends or radiates through the target tissue region. Electrode positioning and energy delivery can be selected and controlled so as to apply a more constant or substantially even voltage field distribution through the target tissue. Energy application can optionally be selected so as to deliver mild and controlled heating of the target tissue to a desired temperature or range.

In one embodiment, the present invention includes a control module assembly and related methods. A control module can include a housing having a first portion forming a plurality of housing channels, each housing channel configured to receive an elongate medical electrode; a circuit board carried by the housing and comprising a plurality of board channels, each board channel configured to receive and electrically couple to an elongate medical electrode, wherein the first portion and the circuit board are coupled such that the housing channels align with the board channels so as to form elongate medical electrode guide passages through the housing and circuit board; and a power source input.

In another embodiment, a control module assembly can include a plurality of electrode guides, e.g., disposed in a housing unit or assembly, configured for controlled positioning in a target tissue an array of electrodes advanced through the guides. The control module further includes a plurality of electrical connects each disposed within an electrode guide and a power source input, and electronics such as computer readable storage media including operating instructions for performing current delivery to a tissue of the patient. Current delivery, in one embodiment, may include differentially activate two or more groups of electrodes positioned in the guides in seriatim; and provide electrical current to the electrodes so as to establish a current flow radially or in a plurality of different directions through a volume of the tissue and to preferentially destroy cancerous or hyperplastic cells in the target tissue region.

A method and structures for delivering an electrical treatment field to a tissue of a patient are provided. A method can include providing a control module assembly and positioning an array of elongate medical electrodes in a target tissue region. Electrode positioning can include advancing an elongate medical electrode through an electrode passage of the control module. A method can further include activating one or more groups of positioned electrodes so as to establish electrical current flow through a volume of the tissue.

In another embodiment, the present invention provides methods and systems for preferential destruction of cancerous cells of a target tissue of a patient. A system can include a control module assembly and a plurality of elongate medical electrodes configured for advancement and positioning through guide passages of the control module and into a target tissue region of the patient.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION OF THE INVENTION

Figure 1A:
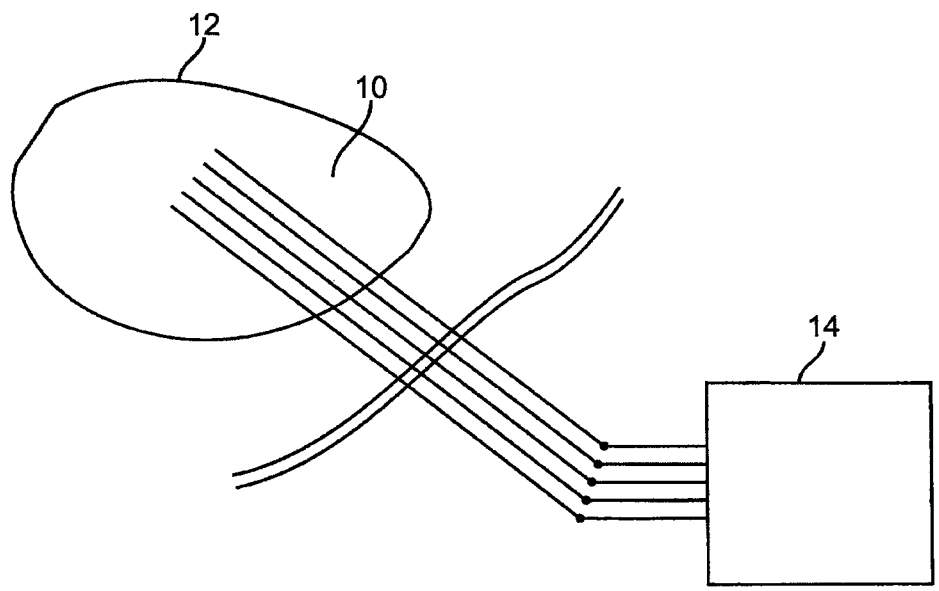
FIGS. 1A and 1B illustrate a system for delivery of electric fields to a tissue of a patient using a plurality or array of electrodes.

The present invention includes systems, methods and devices for applying electric fields to a target tissue using an array of electrodes. Systems and methods as provided herein can be designed and/or utilized for preferential destruction of cancerous cells and tissue ablation and/or controllable tissue heating. In particular, the present invention provides control module systems and assemblies, as well as methodologies for current delivery to a tissue of a patient making use of the provided structures.

Energy application and delivery using control module systems and structures according to the present invention can optionally offer several advantages. First, where tissue heating is desired, energy delivery according to the present invention advantageously allows a more controlled or precise therapeutic energy dose both in terms of delivery of the desired current and resulting hyperthermia effects, as well as more accurate delivery to the target or intended tissue. Current flow can be established between electrodes in a bipolar arrangement, with current flow established and substantially contained between the spaced electrodes. Tissue heating can be more precisely controlled to prevent or minimize excessive or undesirable heating patterns and/or hot spots that can cause unintended damage to healthy or non-target tissues. For example, energy delivery can be selected (e.g., frequency ranges between about 50 kHz to about 300 kHz) such that tissue heating occurs significantly, and in some cases predominately, due to tissue resistance, rather than the high-frictional heating observed at high frequencies (e.g., 500 kHz or greater).

Another optional advantage of the present inventive methods and systems is that energy delivery as described has been observed to be surprisingly effective in preferentially damaging and destroying cancerous cells compared to non-cancerous or healthy cells/tissue. Preferential damage or destruction, as described herein, refers to establishing current flow as described such that cytotoxic effects of energy application are, on average or as a whole, more damaging, destructive and/or lethal to cancerous or hyperplastic cells (e.g., cells exhibiting or predisposed to exhibiting unregulated growth) compared to non-cancerous or healthy cells. In some instances, establishing current flow, which can include induction of mild hyperthermia (e.g., average tissue heating generally below about 50 degrees C.) as described herein is remarkably effective in preferentially destroying cancerous cells with limited or no observable damage to non-cancerous tissues.

Furthermore, and without being bound by any particular theory, electrode configuration and field application as described in certain embodiments (e.g., radially and/or in a plurality of different directions) may take advantage of tumor or mitotic cell physiology to increase treatment effectiveness, and can include a more optimal or effective orientation of the applied field with respect to dividing cells of the target region. For example, energy application can be accomplished such that current fields are substantially aligned at some point during energy delivery with division axes of dividing cells (e.g., cancerous cells), thereby more effectively disrupting cellular processes or mitotic events (e.g., mitotic spindle formation and the like). As cancerous cells are dividing at a higher rate compared to non-cancerous cells, field application in this manner may preferentially damage cancerous cells compared to healthy or non-dividing cells. It will be recognized, however, that energy application according to the present invention likely has several or numerous cytotoxic effects on cells of the target region and that such effects may be cumulatively or synergistically disruptive to a target cell, particularly to cells disposed or pre-disposed to unregulated growth (i.e., cancerous cells). Other cytotoxic or disruptive effects of the energy application as describe herein may occur due, for example, to application of mild hyperthermia (e.g., mild heating of tissue between about 40 to 48 degrees C.; or less than about 50 degrees C.); ion disruption, disruption of membrane stability, integrity or function; and the like.

Various electrode or probe configurations can be utilized according to the present invention. In one embodiment, electrodes can include an array of needle electrodes or elongate medical electrodes, which can be fixed to common support (e.g., housing) or separately positionable and controlled. Such a plurality or array of electrodes can include a straight-needle array including electrically conductive material such as stainless steel, gold, silver, etc. or combination thereof. Electrodes may be at least partially insulated, e.g., along a needle length. For example, a needle may include a non-insulated or minimally insulated energy delivery or conductive portion that is generally located distally along the electrode length, and may further include an insulated portion or length along the needle (e.g., proximally to the non-insulated portion). An insulated portion will be configured to substantially prevent current flow into the tissue at the insulated portion. An electrode can include one or more than one non-insulated or energy delivery portions. An array of straight-needle electrodes can be coupled to a rigid needle support or housing that can ensure correct positioning of each individual needle relative to the others. The needles can be arranged parallel to one another with opposing rows and/or columns of electrodes ensuring the field is delivered to and contained within the target area. Needle length and needle spacing can vary depending on the actual dimensions of the target tissue. Individual needle placement can be guided using imaging (e.g., ultrasound, X-ray, etc.) and relative needle position can be maintained with a rigid grid support (e.g., housing, template, etc.) that remains outside the body. The needle assembly will electrically connect to the control system or module, e.g., via electrical contact point(s), insulated wires, stainless steel couplings, and the like. Other electrode designs and configurations (e.g., deployable, inflatable, etc.) may find use according to the present invention.

Electrodes and probes of the present invention can be coupled to control system or control module designed to generate, deliver, control and optionally monitor the characteristics of the applied field within the specified treatment parameters. In one embodiment, a control system includes a power source, an alternating current (AC) inverter, a signal generator, a signal amplifier, an oscilloscope, an operator interface and/or monitor and a central processing unit (CPU). The control unit can manually, automatically, or by computer programming or control, monitor, and/or display various processes and parameters of the energy application through electrodes and to the target tissue of the patient. While the control system and power source can include various possible frequency ranges, current frequency delivered to target tissue will be less than about 300 kHz, and typically about 50 kHz to about 250 kHz (e.g., 100 kHz). Frequencies in this range have been observed as effective in precisely controlling the energy application to the target tissue, controlling thermal effects primarily to mild thermal application, and preferentially destroying cancerous cells with limited or no observable damage to non-cancerous tissues.

Energy application according to the present invention can be selected to include mild or low levels of hyperthermia. In some embodiments, small changes/elevations in temperature in the target tissue region may occur, but will typically be no more than about 10 degrees C. above body temperature, and may be about 2 degrees to less than about 10 degrees C. above body temperature (e.g., normal human body temperature of about 38 degrees C.). Thus, local tissue temperatures (e.g., average tissue temperature in a volume of treated tissue) during treatment will typically be less than about 50 degrees C., and typically within a range of about 40-48 degrees C. In one embodiment, average target tissue temperature will be selected at about 42-45 degrees C. As target tissue temperatures rise above about 40-42 degrees C. during treatment, the cytotoxic effects of energy delivery on cancerous cells of the target region are observably enhanced, possibly due to an additive and/or synergistic effect of current field and hyperthermic effects. Where mild hyperthermic effects are substantially maintained below about 48 degrees C., the energy delivery according to the present invention appears to more preferentially destroy cancerous cells compared to healthy or non-cancerous cells of the target tissue region. Where energy delivery induces tissue heating substantially in excess of about 45-48 degrees C. (e.g., particularly above 48-50 degrees C.), the preferential cytotoxic effects on cancerous cells may begin to diminish, with more indiscriminate destruction of cancerous and non-cancerous cells occurring. Thus, a significant advantage of treatment methods according to the present invention includes the ability to precisely and accurately control energy delivery and induced hyperthermic effects, such that tissue hyperthermia can be accurately controlled and maintained in a desired temperature range(s)—e.g., temperature ranges selected for more targeted or preferential destruction of cancerous cells compared to non-cancerous cells.

Methods and structures of the present invention can include one or more of various different treatment modalities, including delivery of current or energy selected for low-heat ablation, mild hyperthermia, as well as more traditional forms of thermal ablation. Treatment can be delivered in more or more different treatment phases or stages, and may include a single treatment modality or multiple different treatment modalities delivered in different treatment stages or phases.

Tissue temperatures can be selected or controlled in several ways. In one embodiment, tissue temperatures can be controlled based on estimated or known characteristics of the target tissue, such as tissue impedance and tissue volume, blood flow or perfusion characteristics, and the like, with energy application to the tissue selected to deliver an approximated controlled mild increase in tissue temperature. In another embodiment, tissue temperature can be actively detected or monitored, e.g., by use of a feedback unit, during treatment, with temperature measurements providing feedback control of energy delivery in order to maintain a desired target tissue temperature or range. Temperature control measures can include electronics, programming, thermosensors and the like, coupled with or included in a control unit or module of a system of the invention. Systems may use any combination of techniques described. Further, use of additional heating/cooling means (e.g., temperature controlled air, fluid, radiation, and the like) may be utilized in addition to electrode based heating to facilitate control and delivery of the desired treatment temperature to the target tissue.

Energy application to a target tissue region according to the present application can include delivery of various types of energy delivery. As described, application of generally intermediate frequency range (e.g., less than about 300 kHz) alternating current in the RF range has been observed as effective in establishing mild heating and hyperthermia, as well as current fields in a controlled manner so as to provide a cytotoxic effect, and in some instances, a preferential destructive effect to cancerous cells of a target tissue volume/region. It will be recognized, however, that additional energy applications and/or ranges may be suitable for use according to the present invention, and that systems and methods of the present invention may be amenable to use with other or additional energy applications. For example, energy application can include current flow having frequencies found generally in the RF range, as well as microwave range, including higher frequencies such as 300-500 kHz and above, and may further be amenable to use with direct current applications. Applied current can be pulsed and/or continuously applied, and energy delivery can be coupled with a feedback-type system (e.g., thermocouple positioned in the target tissue) to maintain energy application and/or tissue heating in a desired range.

In certain embodiments, particularly where energy application is selected for lower power delivery/ablation, the control system can be designed to be battery powered and is typically isolated from ground. AC current is derived from the integrated power inverter. An intermediate frequency (e.g., less than 300 kHz; or about 50 kHz to about 250 kHz) alternating current, sinusoidal waveform signal is produced from the signal generator. The signal is then amplified, in one non-limiting example to a current range of 5 mA to 50 mA and voltage of up to 20 Vrms per zone. Field characteristics including waveform, frequency, current and voltage are monitored by an integrated oscilloscope. Scope readings are displayed on the operator interface monitor. An integrated CPU monitors overall system power consumption and availability and controls the output of the signal generator and amplifier based on the treatment parameters input by the operator. The operator can define treatment parameters to include maximum voltage, maximum current or temperature, maximum power, and the like.

Imaging systems and devices can be included in the methods and systems of the present invention. For example, the target tissue region can be identified and/or characterized using conventional imaging methods such as ultrasound, computed tomography (CT) scanning, X-ray imaging, nuclear imaging, magnetic resonance imaging (MRI), electromagnetic imaging, and the like. In some embodiments, characteristics of the tumor, including those identified using imaging methods, can also be used in selecting ablation parameters, such as energy application as well as the shape and/or geometry of the electrodes. Additionally, these or other known imaging systems can be used for positioning and placement of the devices and/or electrodes in a patient's tissues.

Figure 1B:
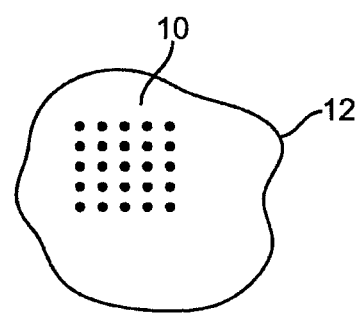

A system and method for delivering electric fields according to the present invention is described with reference to FIGS. 1A and 1B. The system includes a plurality of individual needle electrodes 10 that can be positioned in a target tissue 12, e.g., by making use of a control module assembly or structure as described further herein. Elongated needle electrodes will include a distal portion and a proximal portion. The proximal portion of each electrode will be electrically connected to a system control unit 14 or module, which includes electronics, storage media, programming, etc., as well as a power generator, for controlled delivery of selected electrical fields to the target tissue. In use, a plurality of electrodes will be advanced through the tissue and to a desired position, as shown in FIG. 1A. Electrode positioning can include, for example, insertion and advancement through the skin and through the tissue of the patient. For example, where the target tissue is prostate tissue, electrodes can be advanced percutaneously through the patient's perineum and into the prostate tissue. Electrode positioning and arrangement within the target tissue can be precisely controlled and may occur under the guidance of tissue imaging methodology (e.g., ultrasound imaging, X-ray, CT, etc.). FIG. 1B illustrates a cross-section view of a target tissue 12 having a plurality of positioned needle 10 electrodes according to an exemplary array positioning pattern. Various electrodes and/or patterns, as well as number of electrodes in a particular array, may be utilized an can be selected at least partially based on the intended use as well as clinical considerations.

Figure 2A:
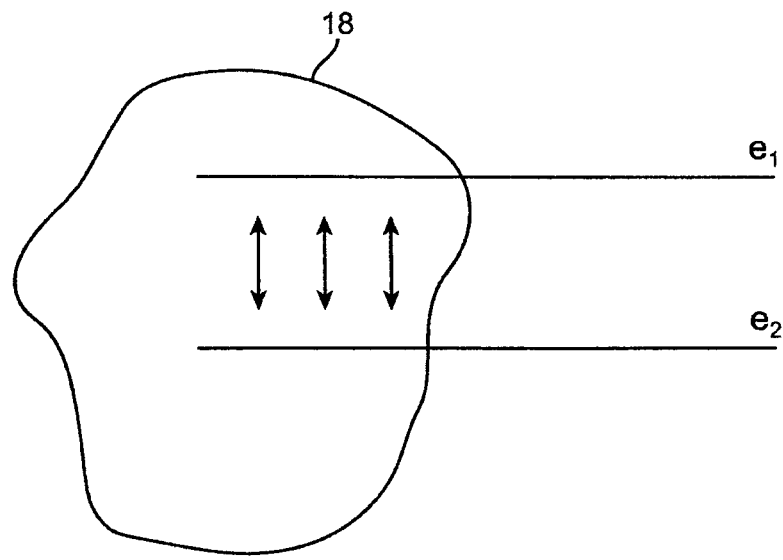
FIGS. 2A through 2D illustrate field delivery in a target tissue according to various embodiments of the present invention.

Energy delivery between positioned electrodes in an array is further described with reference to FIGS. 2A through 3D. Electrodes of an array can be positioned in a target tissue and activated in pairs or groups such that the desired electric field is delivered to the target tissue between the electrodes and, in some instances, in a radial orientation or in a plurality of different directions, or with a field substantially uniform in orientation/direction when applied. FIG. 2A conceptually illustrates establishment of a current field with two spaced electrode elements ($e_1$ and $e_2$) as a basic field delivery unit according to an embodiment of the present invention. As shown, distal portions of two electrodes ($e_1$ and $e_2$) of a plurality positioned in a target tissue 18 and activated as an electrode pair or circuit, with the applied current substantially contained between the two. Thus, electrodes can be activated in a bipolar configuration, with current flowing between electrodes (e.g., between $e_1$ and $e_2$) and the tissue between the electrodes acting as a flow medium or current pathway between the electrodes. Positioning and activation of pairs or relatively small groups of electrodes in this manner allows more precise control of the current and voltage field applied to the tissue, containment of the applied field to the desired location, as well control of heating or limited temperature increase in the target tissue. Several factors may lend to improved control of therapeutic effects of the delivered fields according to the present invention. First, as discussed above activating electrode in a bipolar configuration or so as to form a circuit allows the applied field to substantially be contained within the volume defined by the positioned electrodes. Second, energy delivery can be selected (e.g., frequency ranges between about 50 kHz to about 300 kHz) such that tissue heating occurs predominately due to tissue resistance, rather than the high levels of frictional heating observed at high frequencies (e.g., 500 kHz or greater). High frequency/high friction type heating is typically characterized by significant tissue temperature gradients throughout the treated tissue, with substantially higher tissue temperatures occurring near the electrode. Where high friction type heating is reduced relative to heating occurring due to tissue resistance, a more constant and controlled heating between opposing electrodes can be delivered.

Figure 2B:
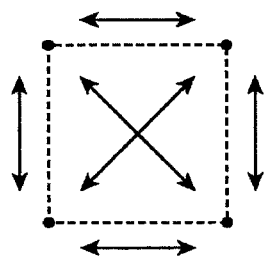
Figure 2C:
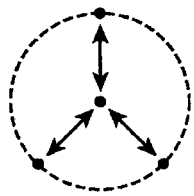
Figure 2D:
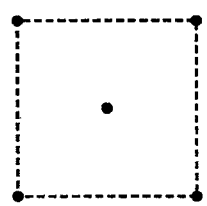
Figure 3A:
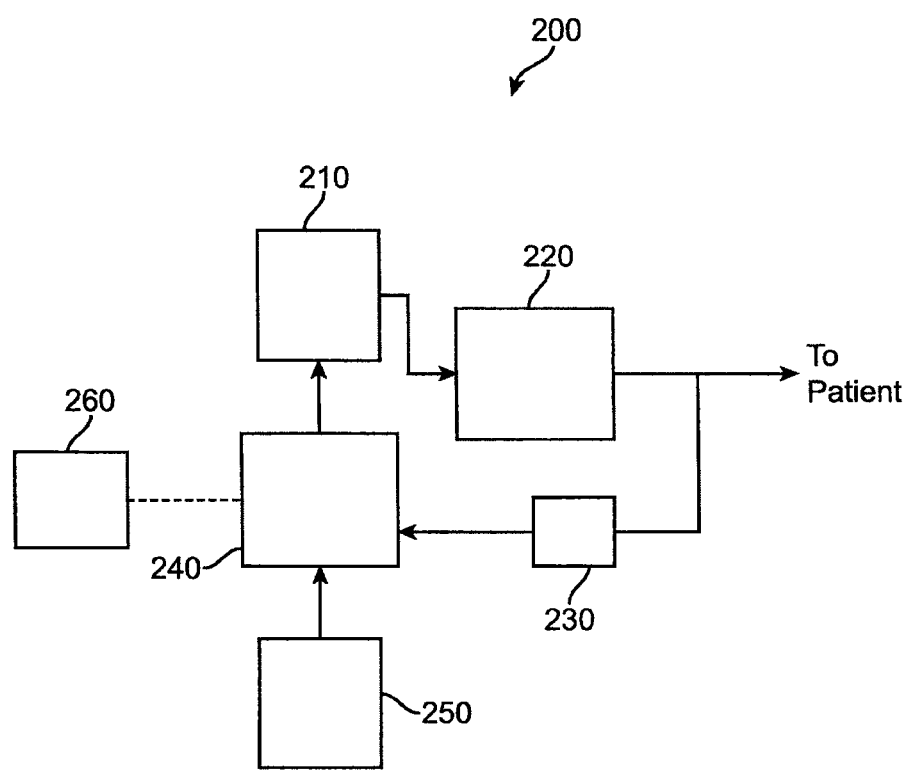
FIG. 3A includes a diagram illustrating a system according to an embodiment of the present invention.
Figure 3B:
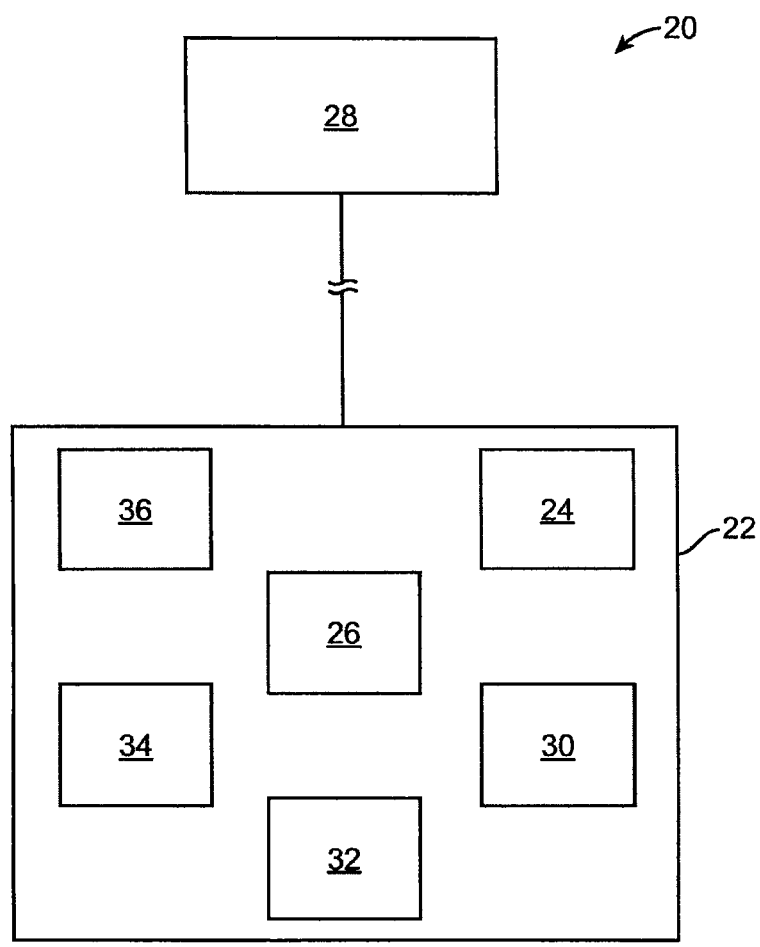
FIG. 3B includes a diagram illustrating a control module assembly or system, according to an embodiment of the present invention.

In some embodiments of therapeutic energy delivery according to the present invention, electrode positioning and/or device configuration advantageously allows delivery of field throughout a target tissue volume in a plurality of different directions, such as radial field orientation and application through the target volume. Again, current delivery as described can be accomplished with use of a control module assembly or structure as described further herein. Besides the simplified electrode pairs as illustrated in FIG. 2A, various electrode group patterns may be selected and utilized for energy delivery. FIGS. 2B through 2D illustrate simplified plan views of electrode positioning and spacing for field application according to exemplary embodiments of the present invention. As shown in FIG. 3B, a simple four electrode box grouping can be selected for use in treatment, with an applied field established and current flowing between a centrally positioned electrode and outer or secondary electrodes positioned spaced from the center electrode. Thus, an exemplary delivery unit can include a centrally located electrode surrounded by spaced electrodes, with the applied field extending between the central electrode and the outer spaced electrodes (see also, FIG. 2D). In this manner, the outer electrodes can essentially define an ablation volume with the inner/central electrode positioned within the volume. Field delivery in this way is advantageously controlled and substantially contained within the ablation volume. Furthermore, field delivery in this manner advantageously allows a current field to be established with current flow in a radial and plurality of different directions through the treatment volume, e.g., extending through or from a flow center located about the centrally positioned electrode. FIG. 2C illustrates exemplary electrode positioning including outer electrodes and an inner or centrally located electrode, for defining a discrete target tissue volume for treatment and application of treatment filed extending radially through the volume. Electrode positioning will not be limited to any particular configuration, and various arrangements will be possible.

In another embodiment of the present invention, systems and methods can include a plurality of electrodes (e.g., needle electrodes) that can be individually advanced and positioned in the target tissue, and electrically activated for energy delivery. In such an embodiment, an array of electrodes can be advanced through the tissue of the patient and electrically activated (e.g., differentially activated) to deliver current field in a plurality of different directions. An array or plurality as described can include various numbers of electrodes, and the selected number can depend, at least partially, on factors such as target tissue characteristics, treatment region, needle size, and the like. An array can include a few to dozens of electrodes. In one example, an array can include about a few electrodes to a few hundred (e.g., 10-100, any number therebetween, or more) electrodes for positioning in the target tissue region. Energy deliver can include activating electrode pairs or groups differentially in a sequence or pattern, which can be selected based on a predetermined treatment plan, actively monitored during energy deliver (e.g., via feedback signal(s)), or a combination thereof.

A system according to an embodiment of the present invention is described with reference to FIG. 3A. The system 200 can include incorporated therewith any device of the present invention for delivery of energy to the patient, and includes a power unit 210 that delivers energy to a driver unit 220 and than to electrode(s) of an inventive device. The components of the system individually or collectively, or in a combination of components, can comprise an energy source for a system of the invention. A power unit 210 can include any means of generating electrical power used for operating a device of the invention and applying electrical current to a target tissue as described herein. A power unit 210 can include, for example, one or more electrical generators, batteries (e.g., portable battery unit), and the like. One advantage of the systems of the present invention is the low power required for the ablation process. Thus, in one embodiment, a system of the invention can include a portable and/or battery operated device. An optional feedback unit 230 measures electric field delivery parameters and/or characteristics of the tissue of the target tissue region, measured parameters/characteristics including without limitation current, voltage, impedance, temperature, pH and the like. One or more sensors (e.g., temperature sensor, impedance sensor, thermocouple, etc.) can be included in the system and can be coupled with the device or system and/or separately positioned at or within the patient's tissue. These sensors and/or the feedback unit 230 can be used to monitor or control the delivery of energy to the tissue. The power unit 210 and/or other components of the system can be driven by a control unit 240, which may be coupled with a user interface 250 for input and/or control, for example, from a technician or physician. The control unit 240 and system 200 can be coupled with an imaging system 260 (see above) for locating and/or characterizing the target tissue region and/or location or positioning the device during use.

A control unit can include a, e.g., a computer or a wide variety of proprietary or commercially available computers or systems having one or more processing structures, a personal computer, and the like, with such systems often comprising data processing hardware and/or software configured to implement any one (or combination of) the method steps described herein. Any software will typically include machine readable code of programming instructions embodied in a tangible media such as a memory, a digital or optical recovering media, optical, electrical, or wireless telemetry signals, or the like, and one or more of these structures may also be used to transmit data and information between components of the system in any wide variety of distributed or centralized signal processing architectures.

Components of the system, including the controller, can be used to control the amount of power or electrical energy delivered to the target tissue. Energy may be delivered in a programmed or pre-determined amount or may begin as an initial setting with modifications to the electric field being made during the energy delivery and ablation process. In one embodiment, for example, the system can deliver energy in a "scanning mode", where electric field parameters, such as applied voltage and frequency, include delivery across a pre-determined range. Feedback mechanisms can optionally be used to monitor the electric field delivery in scanning mode and select from the delivery range parameters optimal for ablation of the tissue being targeted.

Systems and devices of the present invention can, though not necessarily, be used in conjunction with other systems, ablation systems, cancer treatment systems, such as drug delivery, local or systemic delivery, surgery, radiology or nuclear medicine systems, and the like. Another advantage of certain embodiments of the present invention, is that treatment does not necessarily preclude follow-up treatment with other approaches, including conventional approaches such as surgery and radiation therapy. In some cases, treatment according to the present invention can occur in conjunction or combination with therapies such as chemotherapy. Similarly, devices can be modified to incorporate components and/or aspects of other systems, such as drug delivery systems, including drug delivery needles, electrodes, etc.

FIG. 3B illustrates a diagram of a control module assembly, according to an embodiment of the present invention. The assembly 20 includes a housing 22 unit or assembly having a plurality of passages 24 or guides each configured for advancement, positioning, and/or electrical coupling with an elongate medical electrode, e.g., as described above. Carried by the housing is a circuit board 26 having a plurality of openings or channels formed therein, which at least partially form the electrode guide passages. Circuit board channels each include an electrical connect or coupling configured to engage an elongate electrode advanced therein so as to allow electrical coupling for current delivery in active coupling with a power source 28. The power source 28 can be coupled to the circuit board 26 and can be carried by the housing 22 or spaced from the housing 22, as illustrated in FIG. 3B. The assembly may further include electronics for electrical current delivery to a target tissue via an electrode positioned in a guide passage through the housing 22 and circuit board 26 and may include, in addition to electronics and electrical couplings of the circuit board 26, a processer 30 and a computer readable storage media 32 carried by the housing. The computer readable storage media 32 can include one or more instructions which when executed cause a system of the present invention to operably perform one or more steps as described further herein. The assembly 20 can further include a user interface module 34 or components for user interaction and/or control of the assembly. The assembly can further include a display 36 which can include one or more display components. Certain aspects of the assembly are described further herein with reference to exemplary embodiments of the present invention.

Figure 4:
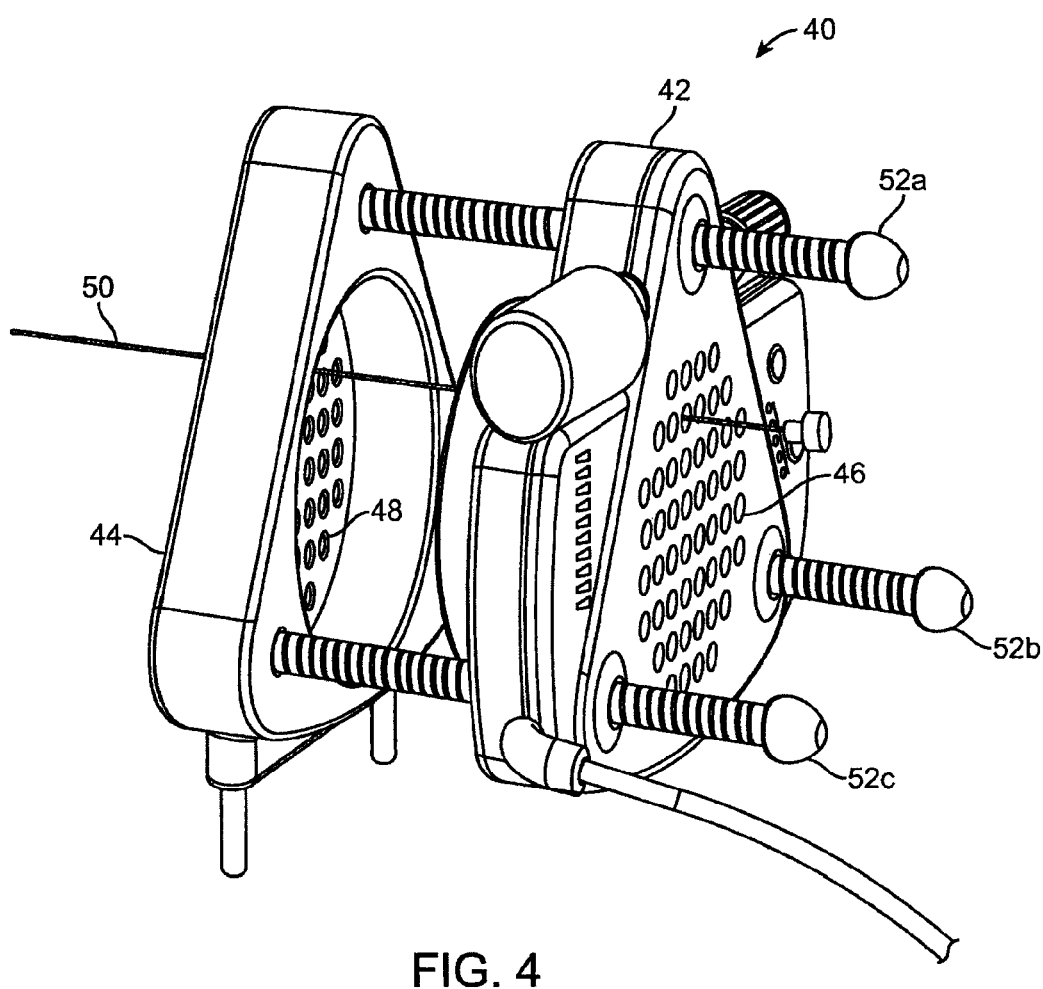
FIG. 4 illustrates a control module assembly and system, including a control module and rear module, according to one exemplary embodiment of the present invention.

FIG. 4 illustrates a control module assembly, according to an embodiment of the present invention. The assembly 40 includes a control module 42 or control module assembly that operably couples to a rear module 44. The control module 42 includes a plurality of electrode guides 46 or elongate medical electrode (e.g., needle electrodes) guide passages each extending through the body of the control module 42, with the plurality of guides configured to electrically connect with each elongate electrode or needle and control positioning a received electrode. The rear module 44 similarly includes a plurality of electrode guides 48 positioned or formed in the rear module 44 such that each of the guides when positioned in substantial alignment corresponds positionally with a guide of the control module 42 as the rear 44 and the control modules 42 are in a coupled arrangement. A single elongated medical electrode 50 is shown positioned through an electrode guide or passage of the control module 42 and through a corresponding electrode guide hole of the rear module 44. Thus, the plurality of electrode guides will be disposed on the control module 42 and configured to control needle alignment in a desired manner and to electrically couple with the electrodes at a proximal portion for energy delivery at a distal portion of the electrodes. The control module 42 further includes electronics and software for electrode activation and energy delivery in a desired manner, e.g. as previously described. The control module 42 is shown coupled to the rear module 44 about a plurality of lead screws 52a, 52b, 52c, that allow control and adjustment of relative spacing or positioning of the modules. The assembly further couples to a power source (not shown), such as a battery pack, as shown in FIGS.

6A and 6B. In use, the assembly can be positioned relative to the patient such that the back plate or side of the rear module is brought into contact with the patient's skin. Needle electrodes are advanced through the electrode guides of the control module and through corresponding guides of the rear module, and through the patient's tissue and to the target site. Electrode activation and energy delivery is selected by the control module.

Figure 5A:
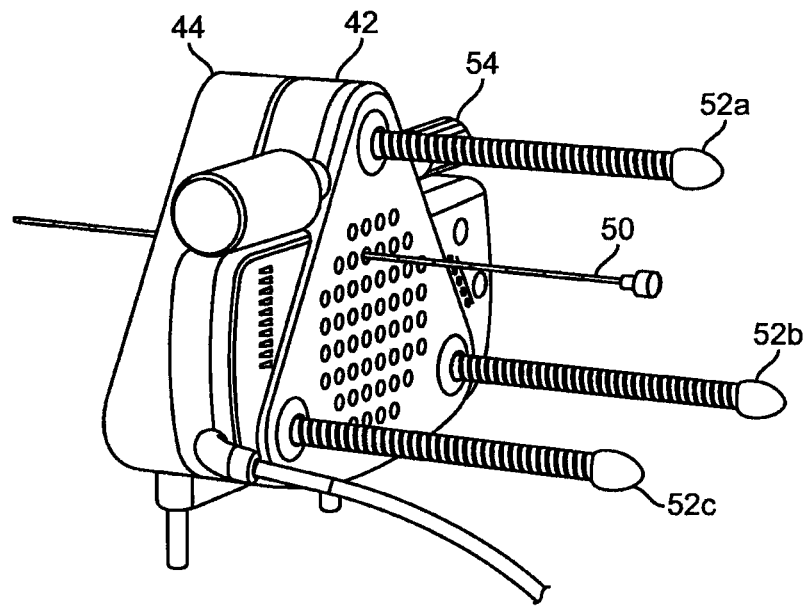
FIGS. 5A and 5B illustrate front-side (FIG. 5A) and back-side (FIG. 5B) of an assembly including a control module and rear module, according to an embodiment of the present invention.
Figure 5B:
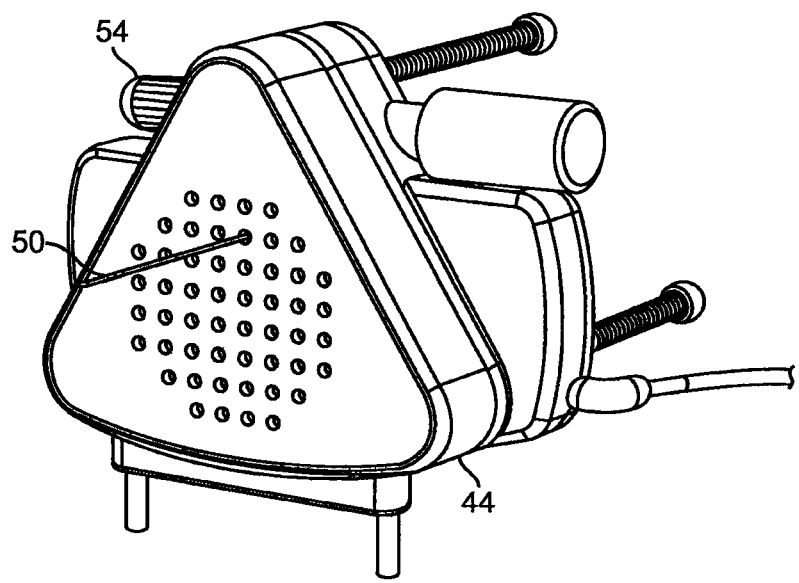

FIGS. 5A and 5B show different views of an assembly including a control module assembly and rear module. The control module 42 and rear module 44 are shown in a more tightly or closely coupled configuration, with the back portion of the control module 42 received by the rear module 44, as the two modules are advanced into contact or approximate contact along the lead screws 52a, 52b, 52c. The assembly can further include a positioning control 54 that when rotated, e.g., by a user, advances the control module along the lead screws. As such, the positioning control and lead screws can be configured for controlling relative distance between the rear module 44 and the control module 42. An elongate medical electrode 50 is shown positioned through a guide passage of the assembly.

Figure 6A:
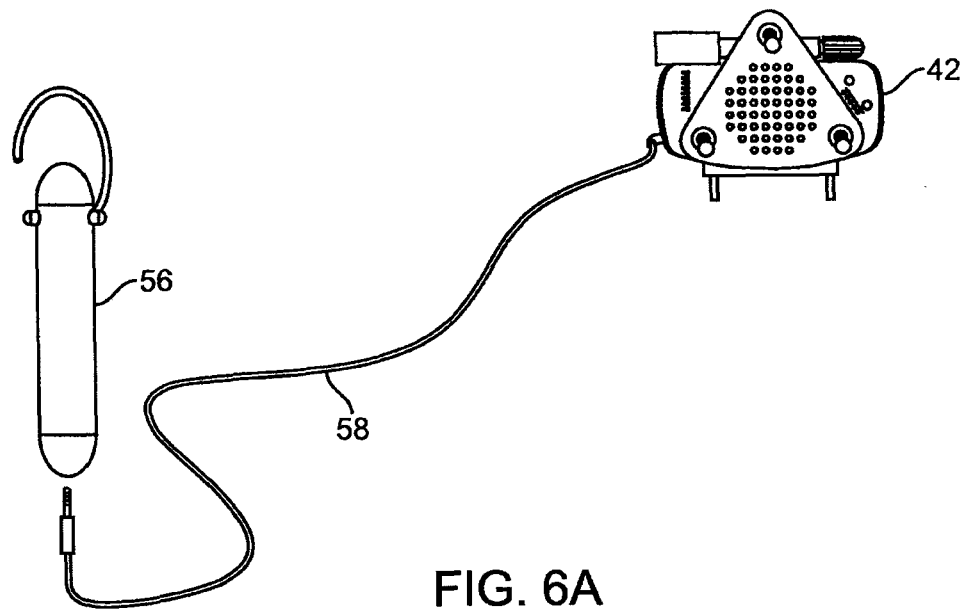
FIGS. 6A and 6B show a control module assembly including a couplable power source, according to an embodiment of the present invention.
Figure 6B:
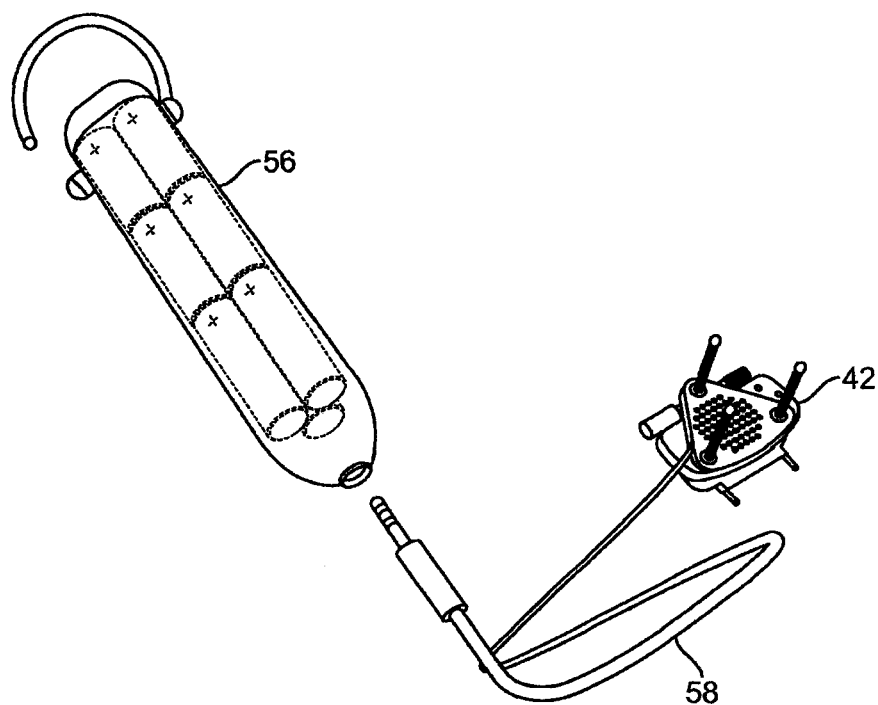

FIGS. 6A and 6B show an assembly including a control module and rear module, and further including a coupled power source. In the illustrated embodiment, the power source 56 includes a battery pack hardwired or coupled to the control module 42 about an elongated electrical connect 58 or wire. The elongated connect optionally, though in some instances advantageously, allows positioning of the power source at a distance relative to the control module, such as positioning of the power source outside a sterile field. While illustrated as a battery pack, various power sources may be utilized.

Figure 7A:
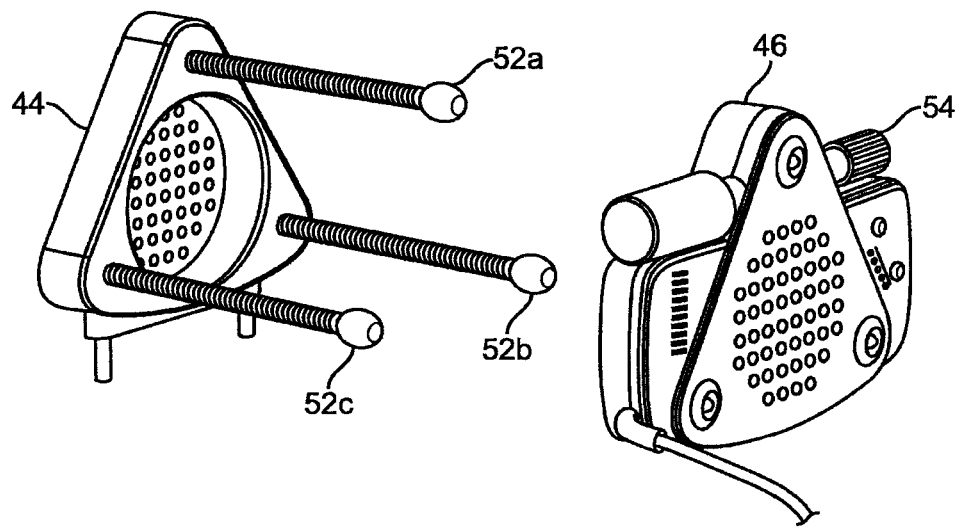
FIGS. 7A and 7B show a control module and rear module in an uncoupled assembly.
Figure 7B:
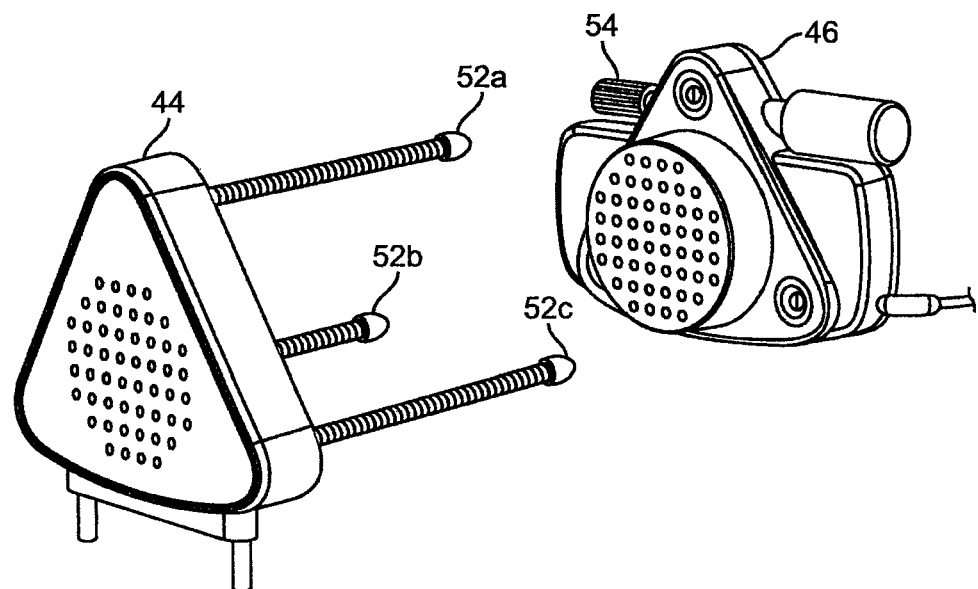

FIGS. 7A and 7B illustrate a control module 42 and rear module 44 in an uncoupled configurations. As above, the control module 42 and rear module 44 can be coupled about lead screws 52a, 52b, 52c, with control 54 allowing adjustment of relative positioning of assembly components.

Figure 8A:
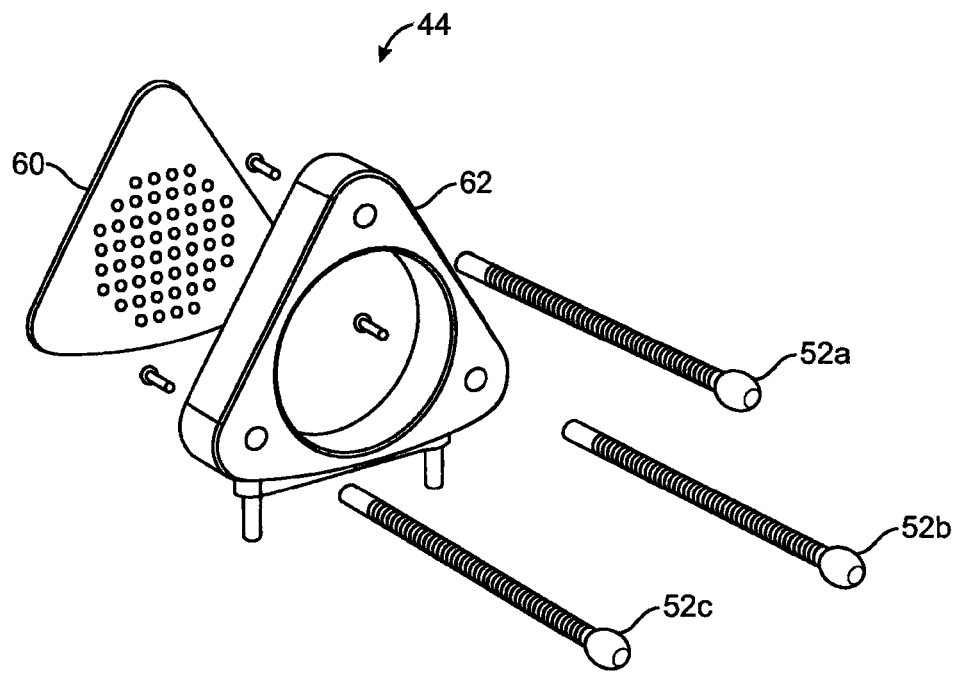
FIGS. 8A and 8B show a exploded views of a rear module assembly, according to an embodiment of the present invention.
Figure 8B:
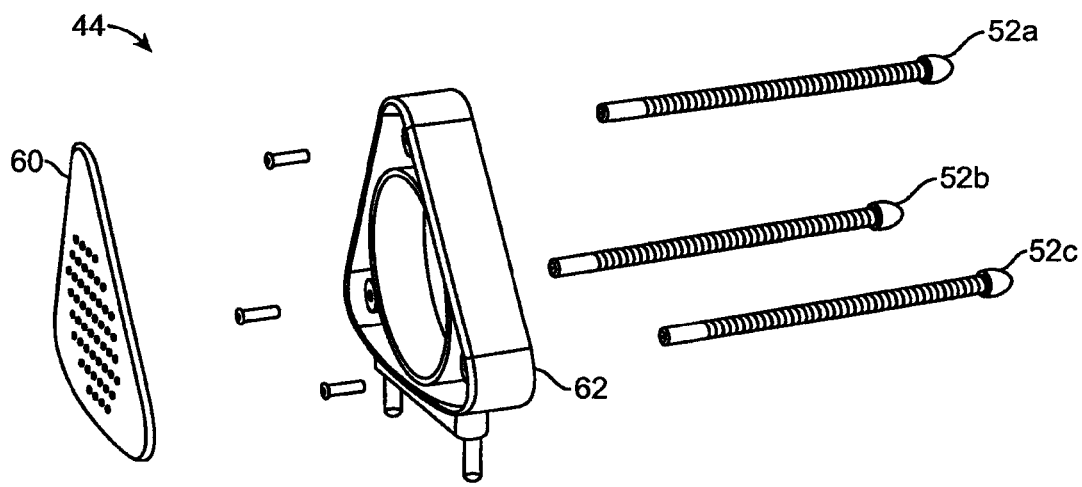

FIGS. 8A and 8B provide an exploded view of the rear module 44 and lead screws 52a, 52b, 52c, according to an embodiment of the present invention. The rear module includes a back plate 60 that couples to a front plate 62. Lead screws 52a, 52b, 52c are shown, which can be received by the front plate 62 of the rear module. As indicated, the back plate 60 includes a plurality of electrode channels or guides, which can be configured to aid in the guidance and positioning of electrodes or can be configured (e.g., oversized) so as to reduce or minimize contribution to needle positioning and alignment. The front plate 62 includes a central opening, which can be sized to match a portion of the control module for male/female type coupling.

Figure 9A:
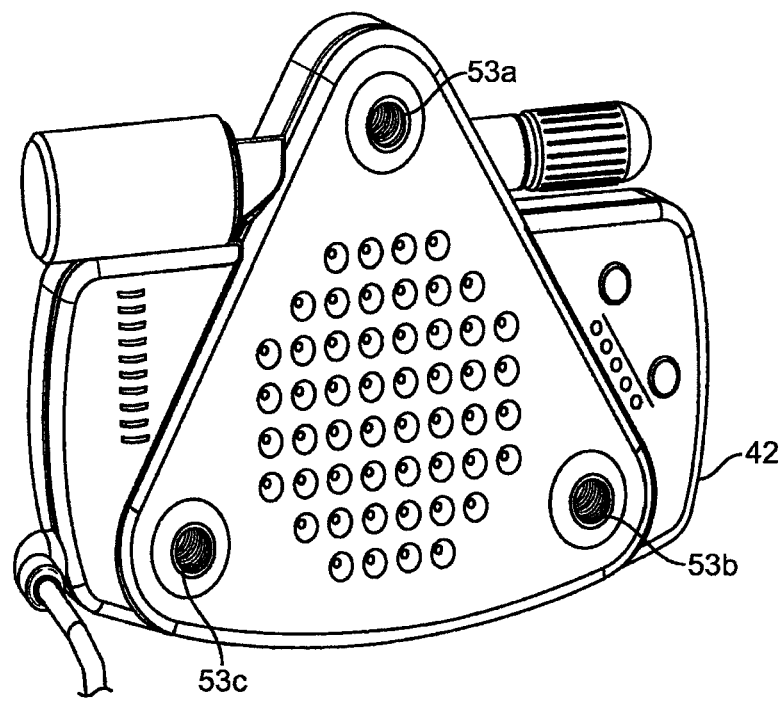
FIGS. 9A and 9B show front side (FIG. 9A) and back side (FIG. 9B) views of a control module, according to an embodiment of the present invention.
Figure 9B:
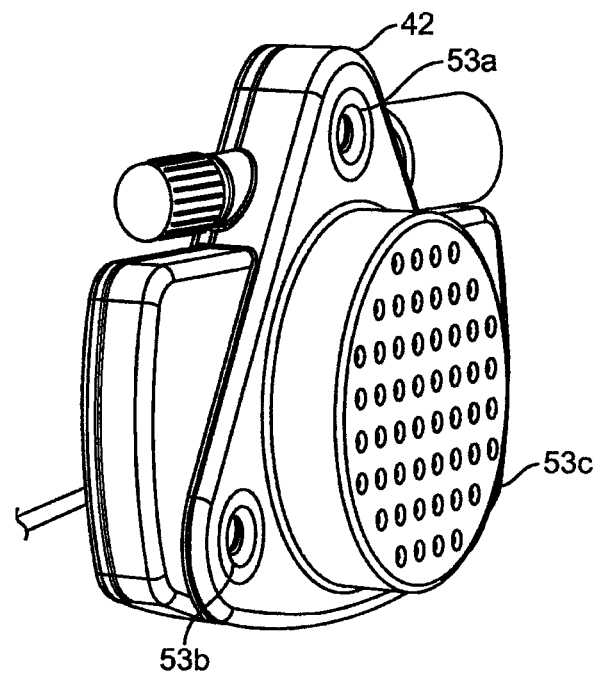

FIGS. 9A and 9B provides back side (FIG. 9B) and front side (FIG. 9A) views of the control module 42, according to an embodiment of the present invention. The control module 42 as shown includes receiving portions 53a, 53b, 53c for lead screws and a mechanical means for controlling advancement along the lead screws (e.g., via manual or motorized advancement). The control module 42 may further include various components for user interface and/or control functions, including power on/of, treatment control or selection, and graphical displays. Display may include a number of LEDs as illustrated, which can include further graphics or design so as to indicate aspects of treatment during use. For example, a display may be configured to indicate treatment (e.g., current delivery) status, length, stage or phase (e.g., in a plurality of stages or phases) The needle guides, as previously indicated, will be sized and configured to electrically connect as well as couple received electrodes and guide needles in a position controlled manner.

Figure 10A:
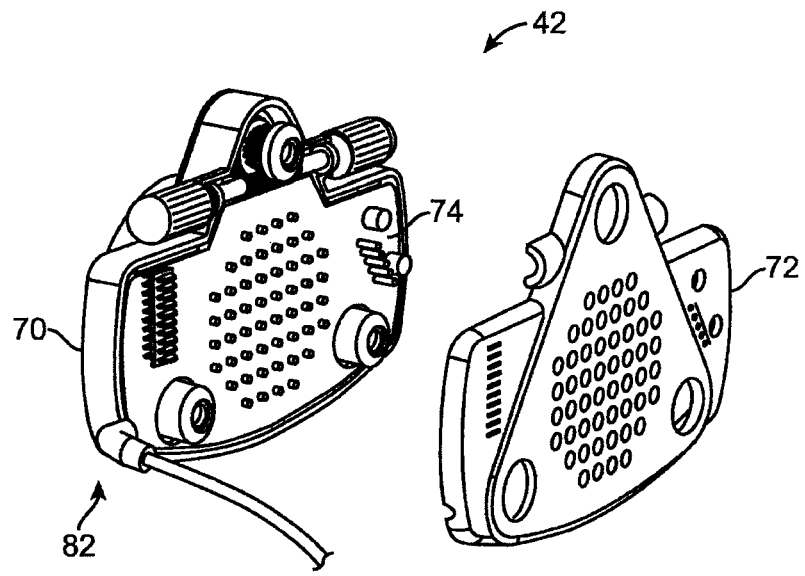
FIGS. 10A and 10B provide partially (FIG. 10A) and more fully (FIG. 10B) exploded views of a control module, according to an embodiment of the present invention.
Figure 10B:
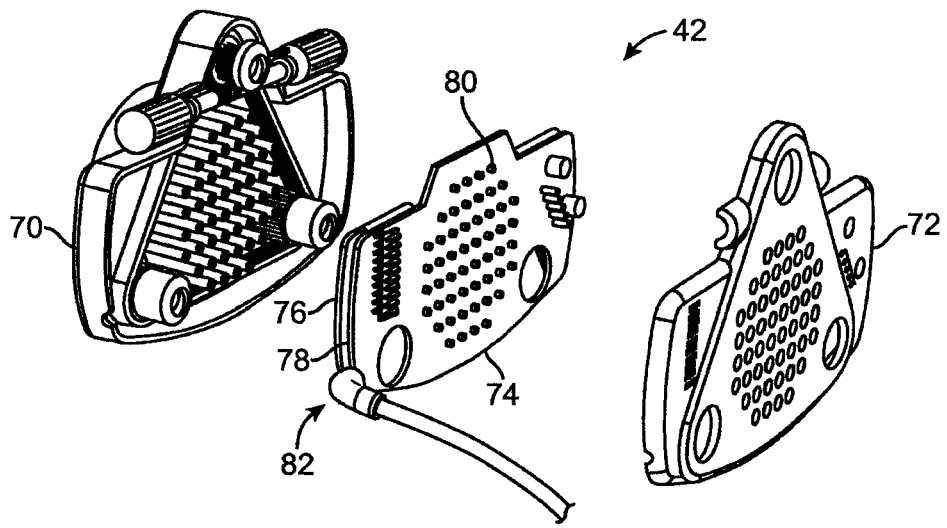

FIGS. 10A and 10B provide partially (FIG. 10A) and more fully (FIG. 10B) exploded views of the control module 42. As shown, the control module includes a back portion 70, a front plate or portion 72, and at least one intermediate portion 74 including electronics (e.g., circuit board, electrical connects, processor, memory, computer readable instructions, etc.) for electrically coupling with the positioned electrodes and providing the desired energy delivery to a target tissue. FIG. 10A shows the control module 42 with the back portion 70 and a circuit board 74 in coupled configuration with the front portion 72 or plate removed in partially exploded view. FIG. 10B shows a more fully exploded view of the control module 42 including a back portion 70, a front portion 72 and a circuit board unit 74 disposed therebetween. As shown and further described herein, each of the front portions and back portions include channels or openings formed therein, where each of the openings or channels is configured to receive an elongate medical electrode according to the uses provided herein. The circuit board 74 further includes one or more board components 76, 78 one or more of which can include channels 80 formed therethrough. Channels in the circuit board unit 74 include an electrical coupling component or conductive couplings that can receive and electrically couple to an elongate medical electrode disposed therethrough. The circuit board 74 can further include additional electronics for permitting or controlling electrical current delivery to a tissue of a patient as described herein. The circuit board 74 is illustrated as including a single piece board component, though it will be recognized that various other configurations or designs may be employed, including multipiece boards or components. The circuit board 74 further includes a power source input or coupling 82 for electrically connecting the circuit board to a power source.

Figure 11:
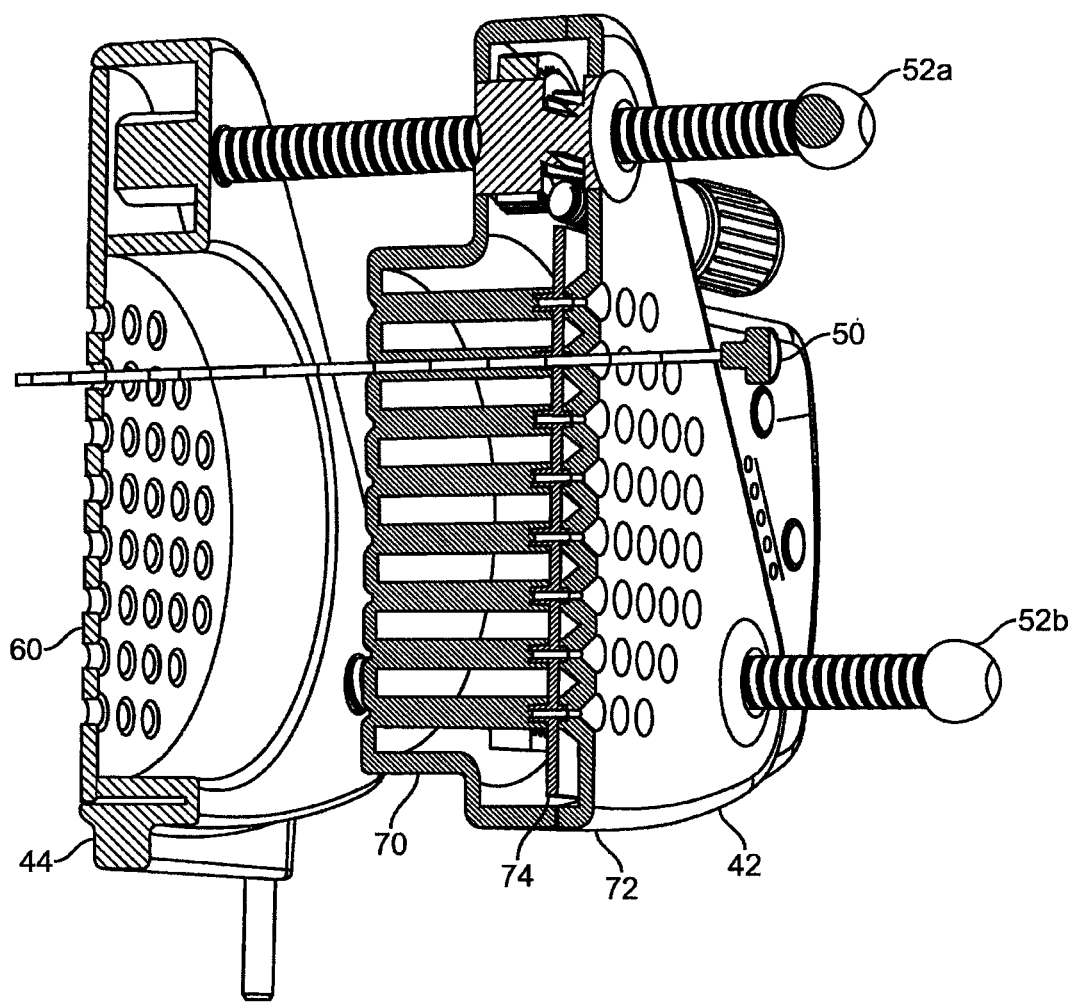
FIG. 11 shows a cross-sectional view of a control module and rear module coupled in a spaced configuration, according to one embodiment of the present invention.

FIG. 11 provides a cross-sectional view of control module 42 and rear module 44 coupled in a spaced configuration, with a single needle electrode 50 extending therethrough. As shown, the needle electrode 50 extends through a guide of the control module and electrically connects to the circuit board 74 of the control module 42 with tight coupling so as to allow controlled placement and positioning of the electrode 50. The electrode 50 extends distally through the back plate 60 of the rear module 44.

Figure 12:
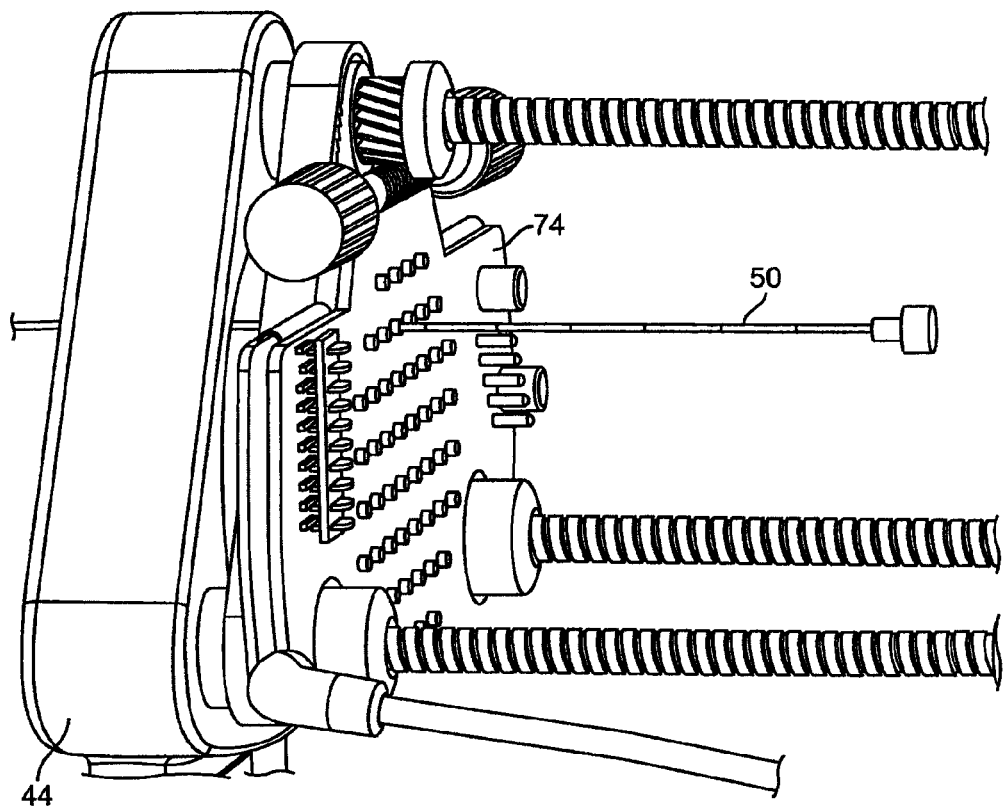
FIG. 12 shows a control module coupled with a rear module, where the front plate of the control module has been removed for illustrative purposes.

FIG. 12 shows the circuit board 74 of the control module 42 more closely coupled with the rear module 44, where the front plate of the control module has been removed for illustrative purposes. A needle electrode 50 is shown advanced through an intermediate portion including circuit board 74 of the control module where electrical coupling with components of the circuit board 74 (e.g., board channels) and electrode positioning can be accomplished.

It is understood that the examples and embodiments described herein are for illustrative purposes only and that various modifications or changes in light thereof will be suggested to persons skilled in the art and are to be included within the spirit and purview of this application and scope of the appended claims. Numerous different combinations are possible, and such combinations are considered part of the present invention.

What is claimed is:

1. A control module assembly, comprising:
 a housing having a back portion and a front portion forming a plurality of housing channels, each housing channel configured to receive an elongate medical electrode, the back portion disposed substantially opposite the front portion;
a circuit board carried by the housing and disposed between the back portion and the front portion, the circuit board comprising a plurality of board channels, each board channel of the circuit board configured to receive and electrically couple to an elongate medical electrode, wherein the back portion, the front portion and the circuit board are coupled such that the housing channels align with the board channels so as to form elongate medical electrode guide passages through the housing and circuit board; and
a power source input configured to couple a power source to the circuit board so as to deliver electrical current to electrical couplings of the board channels.

2. The control module assembly of claim 1, further comprising a display unit carried by the housing, the display unit comprising one or more LEDs.

3. The control module assembly of claim 1, further comprising a user interface carried by the housing.

4. The control module assembly of claim 3, wherein the user interface is operable for user selection or control of current delivery from a coupled power source to one or more electrical couplings and/or duration thereof.

5. The control module assembly of claim 1, further comprising a processor and a computer readable storage media carried by the housing.

6. The control module assembly of claim 5, the computer readable storage media comprising instructions which, when executed, cause the processor to selectively activate one or more guide passages by activating delivery of electrical current to one or more electrical couplings of the board channels.

7. The control module assembly of claim 1, wherein the circuit board comprises a board component having a single piece construction.

8. The control module assembly of claim 1, further comprising a rear module assembly configured for positioning against a patient's tissue.

9. The control module assembly of claim 8, the rear module assembly comprising a back plate having a plurality of openings or channels.

10. The control module assembly of claim 9, wherein the rear module assembly is coupled to the control module assembly such that the back plate openings or channels substantially align with electrode guide passages through the housing and circuit board.

11. The control module assembly of claim 10, wherein the rear module assembly is coupled to the control module assembly about one or more lead screws configured to adjustably control a distance between the rear module and control module.

12. A method of delivering an electrical treatment field to a tissue of a patient, comprising:
providing a control module assembly comprising:
a housing having a back portion and a front portion forming a plurality of housing channels, each housing channel configured to receive an elongate medical electrode, the back portion disposed substantially opposite the front portion;
a circuit board carried by the housing and disposed between the back portion and the front portion, the circuit board comprising a plurality of board channels, each board channel of the circuit board configured to receive and electrically couple to an elongate medical electrode, wherein the back portion, the front portion and the circuit board are coupled such that the housing channels align with the board channels so as to form elongate medical electrode guide passages through the housing and circuit board; and
a power source coupled to the circuit board so as to deliver electrical current to electrical couplings of the board channels;
positioning an array of elongate medical electrodes in a target tissue region, the positioning comprising advancing an elongate medical electrode through an electrode passage of the control module; and
activating one or more groups of positioned electrodes so as to establish electrical current flow through a volume of the tissue.

13. The method of claim 12, wherein a first treatment mode comprises establishing an electrical current flow radially or in a plurality of different directions through the volume of the tissue so as to preferentially ablate cancerous cells in the volume.

14. The method of claim 13, the electrical current flow comprising an alternating current having a frequency of less than about 300 kHz.

15. The method of claim 12, wherein the positioning an array of electrodes in the target tissue region comprises advancing electrodes through the control module passages, through the patient's tissue, and into the target tissue region.

16. The method of claim 12, the activating comprising differentially activating groups of electrodes of the plurality in seriatim so as to establish an electrical current flow in a plurality of different directions through a volume of the target tissue and preferentially destroy cancerous cells in the volume.

17. The method of claim 12, wherein electrical current flow is established in a first treatment mode so as to heat the target tissue to an average temperature of about 40-48 degrees C.

18. A system for preferential destruction of cancerous cells of a target tissue of a patient, comprising:
a control module assembly comprising:
a housing having a back portion and a front portion forming a plurality of housing channels, each housing channel configured to receive an elongate medical electrode, the back portion disposed substantially opposite the front portion;
a circuit board carried by the housing and disposed between the back portion and the front portion, the circuit board comprising a plurality of board channels, each board channel of the circuit board configured to receive and electrically couple to an elongate medical electrode, wherein the back portion, the front portion and the circuit board are coupled such that the housing channels align with the board channels so as to form elongate medical electrode guide passages through the housing and circuit board; and
a power source input configured to couple a power source to the circuit board so as to deliver electrical current to electrical couplings of the board channels; and
a plurality of elongate medical electrodes configured for advancement and positioning through guide passages of the control module and into a target tissue region of the patient.

19. The system of claim 18, further comprising a power source coupled to the electrodes, and a computer readable storage media comprising instructions that, when executed, cause the control system to differentially activate two or more groups of electrodes in seriatim; and provide electrical current to the electrodes so as to establish a current flow radially or in a plurality of different directions through a volume of the tissue and to preferentially destroy cancerous or hyperplastic cells in the target tissue region.

* * * * *